United States Patent [19]

Bithell

[11] 4,348,357
[45] Sep. 7, 1982

[54] PLASMA PRESSURE PULSE STERILIZATION

[75] Inventor: Roger M. Bithell, Richmond, Calif.

[73] Assignee: Motorola, Inc., Schaumburg, Ill.

[21] Appl. No.: 215,597

[22] Filed: Dec. 12, 1980

[51] Int. Cl.$^3$ .......................... A61L 2/14; A61L 2/24
[52] U.S. Cl. ....................................... 422/22; 250/326;
 250/424; 250/492.1; 422/23; 422/33; 250/455.1
[58] Field of Search ...................... 422/22, 23, 26, 33;
 250/326, 455, 492.1, 424, 531

[56] References Cited

U.S. PATENT DOCUMENTS

| 3,701,628 | 10/1972 | Ashman et al. | 422/23 |
| 3,795,483 | 3/1974 | Grafingholt | 422/26 |
| 3,851,436 | 12/1974 | Fraser et al. | 422/22 |
| 3,876,373 | 4/1975 | Glyptis | 250/531 |
| 3,948,601 | 4/1976 | Fraser | 422/23 |
| 3,955,921 | 5/1976 | Tensmeyer | 422/23 |

OTHER PUBLICATIONS

"Guide to Sterility Assurance for Medical Devices", 79-EHD-32; Ministry of Nat'l Health & Welfare; 4-79.

Primary Examiner—Bradley Garris
Attorney, Agent, or Firm—Robert M. Handy

[57] ABSTRACT

A sterilization procedure and apparatus is disclosed in which articles of irregular shape or having long, narrow apertures or cavities may be sterilized at low temperature by being subjected to a plasma whose pressure is varied in a cyclic manner so as to provide forced convection of active species into the apertures, cavities, and crevices of the article to be sterilized.

9 Claims, 3 Drawing Figures

PLASMA PRESSURE PULSE STERILIZATION

TECHNICAL FIELD

This invention relates to the sterilization of various articles in gaseous plasmas, more particularly, to the use of plasma pressure pulses of selected gases to kill harmful microorganisms on medical instruments and other articles of irregular shape and having long narrow apertures therein.

BACKGROUND OF THE INVENTION

In the prior art, many processes have been proposed or used for sterilization such as, for example, wet or dry heat, chemicals, ionizing radiation, electron beams, microwaves, arc discharges, lasers, and plasmas. Heat, penetrating radiation, or chemicals, have been preferred for sterilizing articles of irregular shape which may contain a variety of narrow apertures, holes, or tubes, because of their ability to effectuate sterilization within these types of features.

While wet or dry heat at sufficiently high temperatures is effective for sterilization, its use is restricted to those articles which can remain undamaged by the temperature required (typically 120°–170° C. for 15–60 minutes). Thus, large classes of temperature or moisture sensitive articles cannot be sterilized in this manner.

A particular problem with the use of chemicals, e.g. ethylene oxide, is the length of time required to process a single batch, about 24 hours. In addition, chemical sterilization agents suffer from problems of toxicity and limited shelf life.

Ionizing radiation must be of sufficient high energy to penetrate the articles in order to be effective in sterilization of the complex shapes being considered here. This necessitates the use of x-rays and/or gamma rays, both of which require large and expensive apparatus, and are generally hazardous.

Using a plasma to sterilize articles which contain long, narrow apertures (e.g. blood capillary passages) is disclosed in U.S. Pat. Nos. 3,851,436 and 3,948,601. However, the system and method described therein function by passing a continuous flow of a separately generated plasma through the capillary passages of the articles being sterilized. Such an arrangement is not useful for articles whose openings or apertures are not continuous or which cannot be conveniently arranged to be in series with the gas flow. Additionally, the requirement for a separate chamber for plasma generation is less convenient than an arrangement in which plasma generation and sterilization take place within the same chamber.

Thus, a need exists for an improved method and apparatus which will permit the sterilization of articles of complex shape, and articles containing long, narrow holes, apertures or cavities, particularly where these articles are temperature sensitive. Accordingly, it is an object of this invention to provide an improved apparatus and method for sterilization of objects and articles of irregular shape.

It is an additional objective to provide an improved apparatus and method for sterilizing articles having long, narrow apertures, holes, or cavities therein.

It is a further object of this invention to provide an improved method and apparatus for the sterilization of thermally fragile articles at low temperature.

It is a further object of this invention to provide a plasma sterilization method and apparatus wherein active species of the plasma are carried into the pores, openings, and apertures of the complex shaped article being sterilized.

SUMMARY OF THE INVENTION

The attainment of the foregoing, and other objects and advantages, is achieved through the present invention wherein the article to be sterilized is brought in contact with a low temperature and low pressure plasma whose pressure is varied in a cyclic, although not necessarily periodic, manner between predetermined limits so that active species generated within the plasma are forced into the openings, holes, apertures, and voids, of the subject article. Further, in order to maximize the efficacy of the forced convection of active species into the holes, voids and apertures of the article being sterilized, the duration of pressure rise is arranged to be less than or equal to the duration of the pressure fall. In addition, when sterilizing articles of extreme temperature sensitivity, the plasma can be de-energized during the pressure fall portion of the pressure cycle to reduce heating of the article being sterilized.

BRIEF DESCRIPTION OF THE DRAWINGS

A more complete understanding of the present invention can be obtained by considering the detailed description in conjunction with the accompanying drawings, in which.

DETAILED DESCRIPTION OF THE PREFERRED EMBODIMENT

Figure 1:
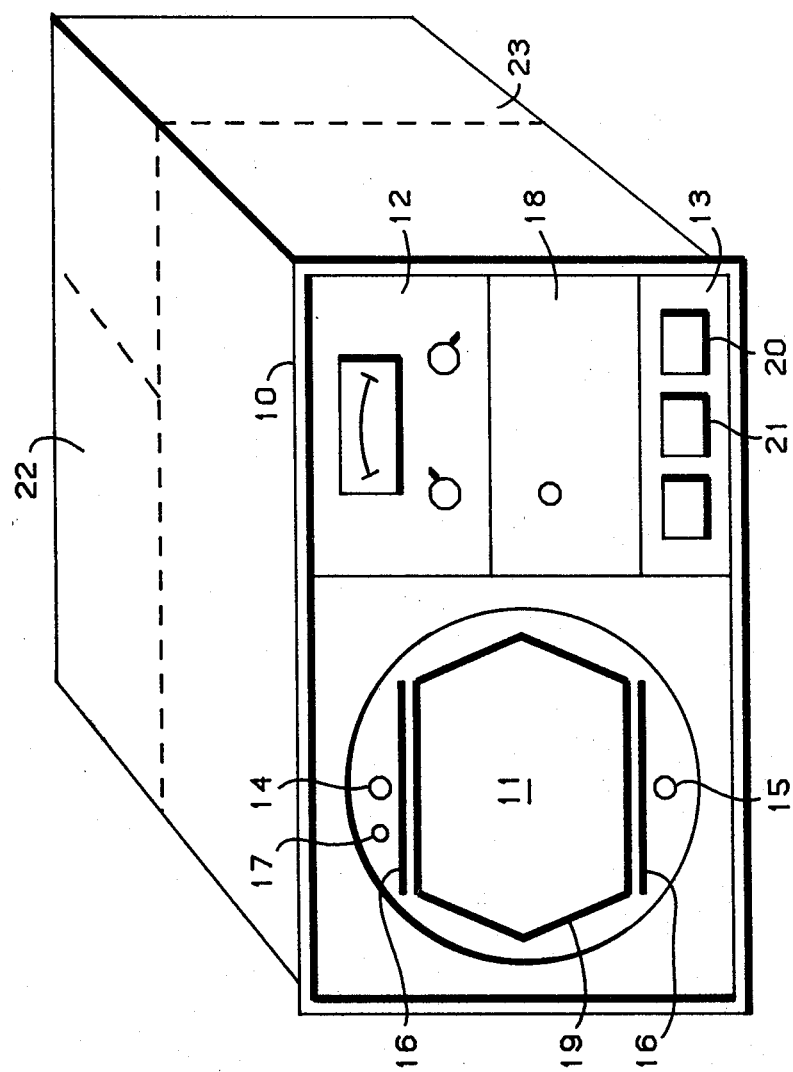
FIG. 1 illustrates a plasma reactor for use in the present invention.

Prior to a detailed description of the present invention, it is desirable to define some terminology. "Sterilization" or "sterile" do not have a universally accepted or absolute definition. Some consider sterile to mean no living thing, i.e. barren. Some consider sterile to mean incapable of reproduction, i.e. inert. Some consider sterile to mean no harmful microorganisms, i.e. benign. Some others consider sterile to mean no foreign matter at all, i.e. clean. There is, however, increasing use now of a probabilistic approach to defining sterility such as is contained in the "Guide to Sterility Assurance for Medical Devices," 79-EHD-32, Ministry of National Health and Welfare, Canada, April 1979. This document defines process and test procedures by which one can attain sterility in the sense of either being benign or inert, and adopts the point of view that sterility in the sense of barren or clean is so difficult to prove as to be moot. Under this approach, then, to "sterilize" or to be "sterile" means being subjected to a process whereby the probability of a contaminant surviving is very low and the micro-organisms on the article have been rendered effectively benign or inert. This is the meaning intended here.

The term "article" as used herein is intended to encompass any object or article, particularly those of complex shape and including those which may have a variety of apertures therein. The term "aperture" as used herein is intended to encompass any cavity, crevice, hole, recess, tube, or other gas permeable opening into or through an article. A "blind aperture" is an aperture, such as for example, a hole or cavity, which has only one opening through which gas may enter or leave the hole or cavity.

Electrical discharges in gases are the customary means of producing plasmas, and can be carried out over ranges of pressures from $10^5$ Torr (13.3 MPa) to $10^{-3}$ Torr (0.133 Pa). For gas at atmospheric pressures (101 kPa) or higher, they are generally called "arcs" and involve very high energy density and gas temperatures $\geqq 1000°$ C. The pressure range of interest here is generally below $10^2$ Torr (13.3 kPa) wherein the average gas temperature in and around the plasma is of the order of a few tens to a few hundred degrees centigrade, depending upon the power levels and the thermal coupling to the exterior environment. In this pressure range a plasma consists of a mixture of free electrons and charged ions and/or free radicals in which atoms or molecules are ionized, disassociated, or excited by an applied electric field, often a radio frequency (RF) field. Ionizing radiation, principally ultra-violet light, is also present. As used herein, "plasma" is intended to mean any portion of the gas which contains electrons, ions, free radicals, dissociated, and/or excited atoms or molecules produced as a result of the electrical discharge, including the accompanying ionizing radiation. It is the ions, free radicals, or other excited or dissociated atomic or molecular species rather than the electrons which are believed to be primarily responsible for the sterilization actions observed, although ultraviolet and other radiation may also contribute. However, the term "active species" as used herein is intended to encompass all those factors which may contribute to the sterilization process.

As illustrated in FIG. 1, plasma reactor 10 comprises chamber 11 of any suitable shape, process monitoring equipment 12 for measuring gas pressure, gas flow and plasma generator power output, process control equipment 13, programmable controller 18, plasma generator 22 and power supplies 23. Process control equipment 13 receives input signals from pressure sensor 17 and process monitoring equipment 12, and activates pressure cycle control 21 and RF plasma generator control 20 under the direction of programmable controller 18 to achieve any desired sequence of pressures, gas flows, and plasma generation periods. Pressure regulators and valves are used in the gas supply and exhaust lines for control purposes and a vacuum pump is used. A microprocessor is a convenient and well known per se programmable controller. In the particular embodiment illustrated in FIG. 1, chamber 11 comprises a cylindrical or polygonal section made from any suitable material such as aluminum or quartz. Interior to chamber 11 are gas supply means 14, exhaust means 15, and pressure sensor 17. Within chamber 11, the plasma is induced by one or more RF electrodes 16 of plasma generator 22. The article to be sterilized is placed in support 19 so as to be within or in contact with the the plasma.

Figure 2:
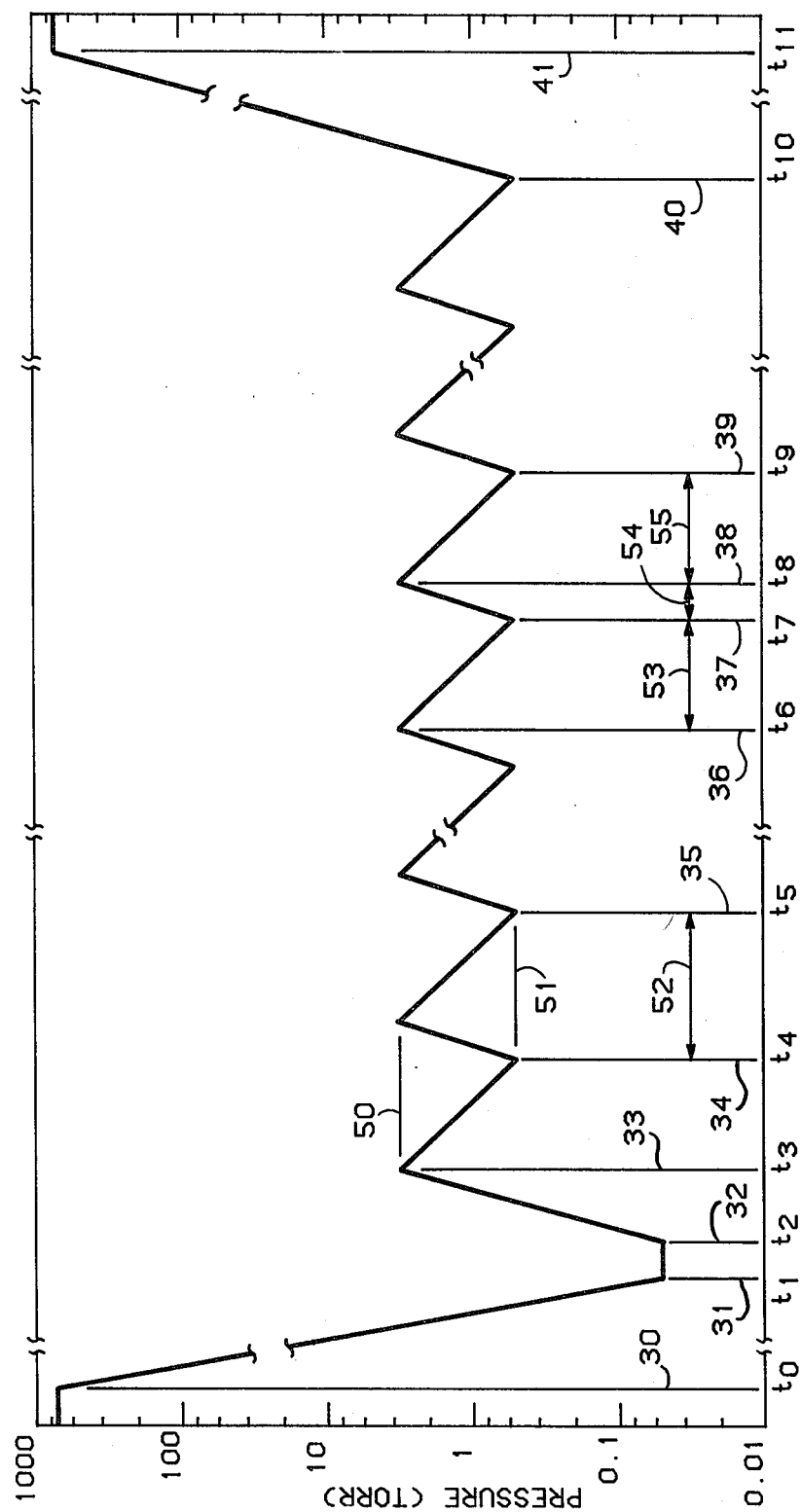
FIG. 2 illustrates in schematic form a sequence of pressure changes as a function of time in accordance with the present invention.

FIG. 2 illustrates in schematic form the pressure variations taking place within the reaction chamber during a preferred embodiment of the method of this invention and serves to provide a framework for the description of the operating procedures important to this invention. In the practice of the method of this invention, the articles to be sterilized are placed within the reaction chamber 11 of plasma reactor 10 (FIG. 1) which is then closed to form a substantially gas-tight seal. At time $t_0$ (line 30 of FIG. 2), the reaction chamber (hereinafter called plasma reactor) is evacuated to a pressure less than 1 Torr (0.13 kPa), typically 0.05 Torr (6.7 Pa), in order to degas the article and the chamber. The degassing step removes the original or starting ambient atmosphere from any apertures of the article as well. This point is reached at time $t_1$ (line 31). A reactant gas, typically oxygen, is admitted to the plasma reactor and at approximately the same time $t_2$ (line 32), the plasma generator is turned on to form an AC glow discharge plasma at approximately 13.56 megahertz and typically 200–350 watts, although lower and higher powers can be used. The pressure of the plasma is increased to an upper pressure limit shown by line 50 which may be as high as 100 Torr (13.3 kPa), but is more typically 1–10 Torr (0.13–1.3 kPa), at which time $t_3$ (line 33) the reactant gas supply is shut off and the plasma reactor pressure allowed to fall in response to the continuing action of the vacuum pump until a lower pressure limit shown by line 51 is reached. The lower pressure limit (line 51) may be as small as can be obtained with a vacuum pump of economical size, which for the equipment used in these experiments was 0.05 Torr (6.7 Pa), but is typically 0.25–1.0 Torr (0.033–0.13 kPa), this point being reached at time $t_4$ (line 34), whereupon reactant gas is readmitted and a pressure rise-pressure fall cycle 52 (time $t_4$, line 34 to time $t_5$, line 35) repeated. Since some pressure overshoot occurs, the gas supply may be turned on or off before the desired pressure limits are actually reached. The pressure is cycled between the upper pressure limit (line 50) and the lower pressure limit (line 51) with the plasma generator energized continuously until time $t_6$ (line 36).

With the long, narrow apertures being considered here (length to width greater than 20:1, and widths less than 5 mm), it is believed that the primary generation of active species occurs external to the apertures, although with optically transparent materials some sterilization action may be contributed by the ionizing radiation inevitably present in the RF plasma. The active species being generated exterior to the aperture are carried into the aperture by the rising portion of the pressure pulse, i.e. the "pressure-rise interval". The active species have a small but finite lifetime, so the rising pressure pulse should be as short as is practically convenient so that the maximum number of active species survive during the time necessary to carry them into the interior of the apertures. Pressure-rise intervals as long as 60 seconds are believed to be effective in promoting sterilization of long narrow apertures, but shorter intervals (e.g. <10 seconds) are desirable.

During the falling pressure portion of the pressure pulse, i.e. the "pressure-fall interval", active species are no longer being pushed into the interior of the holes and apertures within the sample, and this portion of the cycle should be slow relative to the lifetime of the excited species so as to allow time for the sterilization reactions to take place within the apertures. As a matter of practicality, this portion of the cycle is usually determined by the capacity of the vacuum pump used and the size of the reaction chamber.

It can be shown that the effective length L of a blind aperture penetrated by the active species in response to the pressure change is given approximately by $L = d(P_2/P_1)$ where $P_2$ is the upper pressure limit (line 50), $P_1$ is the lower pressure limit (line 51) and d is the effective diffusion length of the active species, believed to be at least 1-2 cm for 2-5 mm diameter apertures. The effective diffusion length d is defined as that distance along an aperture of a given width through which active species will diffuse to produce sterilization for a given temperature and time. If the aperture has multiple openings then L corresponds to the length to the most interior point.

Thus to maximize L, the ratio $P_2/P_1$ should be as large as possible within the practical limits imposed by pump speed and total available run time. However significant improvement over the behavior of substantially steady plasmas is obtained for values of $P_2/P_1 > 2$.

During the time period $t_2$ to $t_6$, the temperature of the article being sterilized increases. The higher the temperature, the shorter the required sterilization time. There are many articles which are relatively insensitive to temperature and are able to withstand the modest temperature achieved in the plasma without harm. In these cases continuously energized pressure rise-fall cycle 52 is continued until sterilization is complete at time $t_{10}$ (line 40) where upon the system is returned to atmospheric pressure (101 kPa) (line 41) and opened.

However, many medically useful articles have maximum temperature limits which are quite low, for example, 70° C. or less. The temperature that will be reached by an article is a function of the input power, the pressure cycle, the material composition and properties, and other factors and can be readily determined by experiment for any combination of operating conditions. When sterilizing temperature sensitive, thermally fragile articles, once they have completed a "pre-heat" cycle and reached the desired operating temperature at time $t_6$ (line 36), the plasma generator is shut off during pressure-fall interval 53 (time $t_6$, line 36 to time $t_7$, line 37) of the cycle and re-energized during pressure-rise interval 54 (time $t_7$, line 37 to time $t_8$, line 38) of the cycle. Pressure-rise portion 54 should be <60 seconds, typically 0.2-0.3 seconds or less, and pressure-fall interval 53 or 55 (time $t_8$, line 38 to $t_9$, line 39) may be of any convenient length, typically 5 seconds, but in any case not less than pressure-rise interval 54. With the RF plasma generator shut off during the pressure-fall interval, the total heat input to the article being sterilized is reduced in proportion to the plasma generator duty cycle, without any significant reduction in the number of active species, being forced into the interior of the various apertures in the sample.

Pressure-rise, power-on interval 54 and pressure-fall, power-off interval 55 are repeated until the sterilization run has been completed at time $t_{10}$ (line 40) whereupon the vacuum pump is valved off, the plasma generator turned off, the plasma reactor returned to atmospheric pressure (101 kPa) at time $t_{11}$ (line 41), and the articles removed. The time $t_{10}$ necessary to achieve sterilization can be readily determined by experiment for any given sample configuration, reactant gas mixture, desired pre-heat temperature, pressure limits and rise-fall intervals, plasma power level, and shape of article being sterilized. The pressure limits (lines 50-51) and intervals 52-55 may be varied during the run if desired.

To determine the sterilization efficacy of various plasma treatments, the contaminant Bacillus Subtilis was applied to sterile test articles in sufficient quantity to give $10^5$-$10^6$ active bacillus spores (colony forming units) per sample, then dried overnight at 50° C. Following exposure to the plasma, the test samples and control samples (i.e. without plasma exposure) were cultured using agar nutrient or equivalent and incubated by methods well known per se in the art, typically at 37° C. for 36 hours. Thereafter, if growth colonies were present they could be clearly seen and counted, and each colony was considered to represent one remaining active spore (colony forming unit). When no spores were observed, the article was considered sterile, that is, the probability of a containment surviving was less than $10^{-3}$ to $10^{-4}$ percent.

Figure 3:
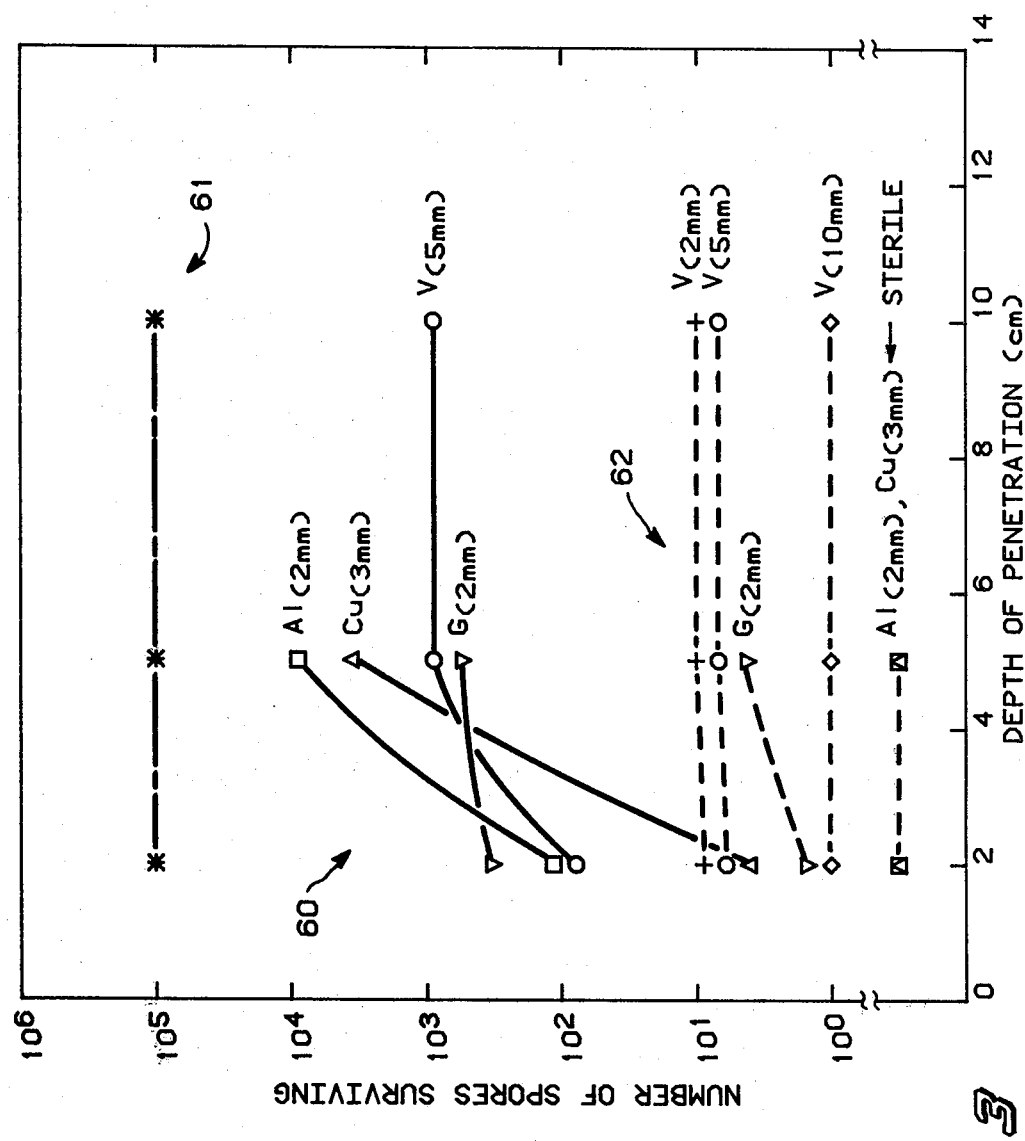
FIG. 3 shows the results of plasma treatment of hollow tubes of different materials compared to control samples in terms of the number of culture forming spores inside the tubes which survive a given treatment, versus the distance from the open end of the tube, for several treatments.

FIG. 3 shows the results of experimental tests made on small bore tubes of a variety of materials, first in a steady (non-pulsed) oxygen plasma operating at 250 watts, a pressure of 2 Torr (0.27 kPa) and sample temperature of 104° C. for two hours. These data are shown by the solid lines 60 in the upper half of FIG. 3 wherein aluminum (Al), copper (Cu), glass (G) and vinyl (V) tubes of 2-5 mm inside diameter were exposed to the plasma. Control samples otherwise identical but not subjected to the plasma showed colony forming spore counts 61 of the order of $10^5$ or higher. After exposure to the steady plasma, substantial numbers of colony forming spores survived, increasing as a function of the depth into the narrow tubes, showing that simple diffusion of active species into the tubes would not be adequate to guarantee sterilization of the interiors, particularly where length/width ratios exceeded about 5.

A second run 62 (dashed lines of FIG. 3) was made at 350 watts for six hours at a sample temperature of 70° C., where plasma pressure was pulsed between 0.25 and 0.95 Torr (0.33-0.126 kPa), rise time (interval 54) was 9 seconds and fall time (interval 55) was 55 seconds. A substantial reduction in residual spore count was obtained in all tubes. The aluminum and copper tubes were sterile and the vinyl and glass tubes showed 10 or less surviving colonies throughout their entire length, including those in which the length/width ratio was as high as 50. The efficacy of the plasma pressure pulse sterilization method compared to non-pulsed plasma sterilization is clearly shown. In other experiments it has been found that tubes up to 20 cm in length and with bores of 2 mm inside diameter or larger are rendered sterile in run times of 6 hours or less for all of these materials.

Gases containing oxygen, nitrogen, helium, argon, and freon have been used successfully. The choice of a particular gas or gas mixture is not based solely upon its ability to yield active species capable of sterilization, but also based upon the other effects which it may exhibit or changes which it may produce in the articles being sterilized. For example, nitrogen has been found to discolor certain plastics. Unlike contrary reports in the prior art, oxygen was found in the present invention to be an effective sterilization agent with few side effects.

Thus, it is apparent that there has been provided in accordance with this invention an improved apparatus and method for sterilizing articles of irregular shape, for sterilizing articles with long narrow apertures therein, for sterilizing thermally fragile articles at low temperature and further for sterilizing articles of complex shape by pumping active species into the apertures therein. Having thus described the invention, it will be apparent to those of skill in the art that various modifications can be made within the spirit and scope of the present invention.

For example, the particular gas to be used, the operating pressure and range through which the pressure is cycled, the duration of the pre-heat cycle and the sample temperature utilized, and the time durations of various portions of the overall sterilization process, are parameters to be decided by the user depending upon the particular articles being sterilized. Accordingly, it is intended to encompass all such variations as fall within the spirit and scope of the invention.

I claim:

1. A process for sterilizing an article having at least one aperture therein, in a plasma reactor, and without gas flow passing unidirectionally through said aperture comprising the steps of:

supplying a reactant gas appropriate for plasma generation;

varying pressure of said reactant gas within said plasma reactor up and down in a cycle over a prescribed range, each said cycle comprising a pressure-rise interval less than 60 seconds and a pressure-fall interval longer than and following each pressure-rise interval;

energizing a plasma reactor generator during at least the pressure-rise interval to create active species for sterilization; and continuing for a sufficient time such that a contaminant on said article has a very low probability of survival.

2. A process for sterilizing at least one article having a blind aperture therein, comprising the steps of:

placing said article in a plasma reactor so as to be in contact with a plasma subsequently formed therein;

evacuating said reactor after said article is placed therein;

supplying a reactant gas at a pressure less than atmospheric appropriate for plasma generation;

varying pressure of said reactant gas within said plasma reactor up and down in a cycle over a prescribed range less than atmospheric, each said cycle comprising a pressure-rise interval less than about 60 seconds and a pressure-fall interval longer than and following said pressure-rise interval;

energizing a plasma generator during at least the pressure-rise interval to create active species for sterilization which penetrate said blind aperture; and continuing for a sufficient time such that a contaminant on said article and in said blind aperture has a very low probability of survival.

3. The process of claim 1 or 2 wherein said plasma generator is additionally energized during at least one pressure-fall interval.

4. The process of claim 3 wherein said plasma generator is energized during sufficient pressure-rise and pressure-fall intervals to heat said article to a predetermined temperature, and thereafter de-energized during at least one pressure-fall interval to conserve energy and limit further heating of said article.

5. The process of claim 4 wherein said reactant gas contains oxygen.

6. The process of claim 1 or 2 wherein said prescribed range has a lower pressure limit $P_1 > 0.05$ Torr (6.7 Pa) and upper pressure limit $P_2$ given by a relation $P_2/P_1 > L/d$ where L is an effective interior length of an aperture and d is an effective diffusion length for said active species.

7. The process of claim 1 or 2 wherein said prescribed range has an upper pressure limit $P_2 < 100$ Torr (13.3 kPa) and lower pressure limit $P_1$ given by a relation $P_2/P_1 > L/d$ where L is an effective interior length of an aperture and d is an effective diffusion length for said active species.

8. The process of claim 1 or 2 wherein said pressure-rise interval is less than about 10 seconds, and said pressure-fall interval is longer than said pressure-rise interval.

9. The process of claim 8 wherein said pressure-rise interval is less than 10 seconds, and said pressure-fall interval is longer than said pressure-rise interval.

* * * * *

UNITED STATES PATENT AND TRADEMARK OFFICE
CERTIFICATE OF CORRECTION

PATENT NO. : 4,348,357
DATED : September 7, 1982
INVENTOR(S) : Roger M. Bithell

It is certified that error appears in the above-identified patent and that said Letters Patent is hereby corrected as shown below:

On the title page Assignee should read

-- Tegal Corporation, Richmond, Calif. --.

Claim 9, line 2, "10 seconds" should read -- about 2 seconds --.

Signed and Sealed this

Fifteenth Day of March 1983

[SEAL]

Attest:

GERALD J. MOSSINGHOFF

Attesting Officer

Commissioner of Patents and Trademarks